(12) United States Patent
Ishikawa

(10) Patent No.: US 6,790,216 B1
(45) Date of Patent: Sep. 14, 2004

(54) ULTRASONIC TREATMENT APPLIANCE

(75) Inventor: Manabu Ishikawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/170,264

(22) Filed: Oct. 13, 1998

(30) Foreign Application Priority Data

Oct. 15, 1997 (JP) ............................................. 9-282098

(51) Int. Cl.$^7$ ......................................... A61B 17/32
(52) U.S. Cl. ....................................... 606/169; 606/207
(58) Field of Search ............................. 601/2; 606/169, 606/170, 171, 205, 206, 207, 210

(56) References Cited

U.S. PATENT DOCUMENTS

| | | | |
|---|---|---|---|
| 5,322,055 A | | 6/1994 | Davison et al. ................ 601/2 |
| 5,562,693 A | * | 10/1996 | Devlin et al. ............... 606/169 |
| 5,868,786 A | * | 2/1999 | DiFrancesco ............... 606/170 |
| 5,893,835 A | * | 4/1999 | Witt et al. ..................... 601/2 |
| 5,908,420 A | * | 6/1999 | Parins et al. ................ 606/170 |
| 5,980,510 A | * | 11/1999 | Tsonton et al. ............. 606/169 |
| 6,063,050 A | * | 5/2000 | Manna et al. |

FOREIGN PATENT DOCUMENTS

| | | | |
|---|---|---|---|
| JP | 08275949 | * | 10/1996 |
| JP | 8-275949 | | 10/1996 |
| JP | 8-275950 | | 10/1996 |
| JP | 9-38099 | | 2/1997 |
| JP | 09038099 | * | 10/1997 |
| JP | 10-5236 | | 1/1998 |
| JP | 10-127654 | | 5/1998 |

* cited by examiner

*Primary Examiner*—Danton D. DeMille
(74) *Attorney, Agent, or Firm*—Armstrong, Kratz, Quintos, Hanson & Brooks, LLP.

(57) ABSTRACT

An ultrasonic treatment appliance consists of: an ultrasonic transducer unit having an ultrasonic transducer, which produces ultrasonic waves, incorporated in a hand-held piece; a probe connected to a horn for amplifying ultrasonic waves produced by the ultrasonic transducer, and serving as a vibration transmission member; a treatment member located at the distal end of the probe, having an ultrasonic treatment surface that is parallel to the longitudinal axial direction of the probe and is flat, exhibiting a larger section modulus at the proximal end thereof than at the distal end thereof, and having ultrasonic waves transmitted thereto; a clamping member, opposed to the treatment member, for clamping a living tissue in cooperation with the treatment member; and a clamping manipulation member for use in moving at least one of the treatment member and clamping member so as to clamp a living tissue between them. Owing to these components, the ultrasonic treatment appliance can offer stable treatability and enjoy excellent durability.

7 Claims, 6 Drawing Sheets

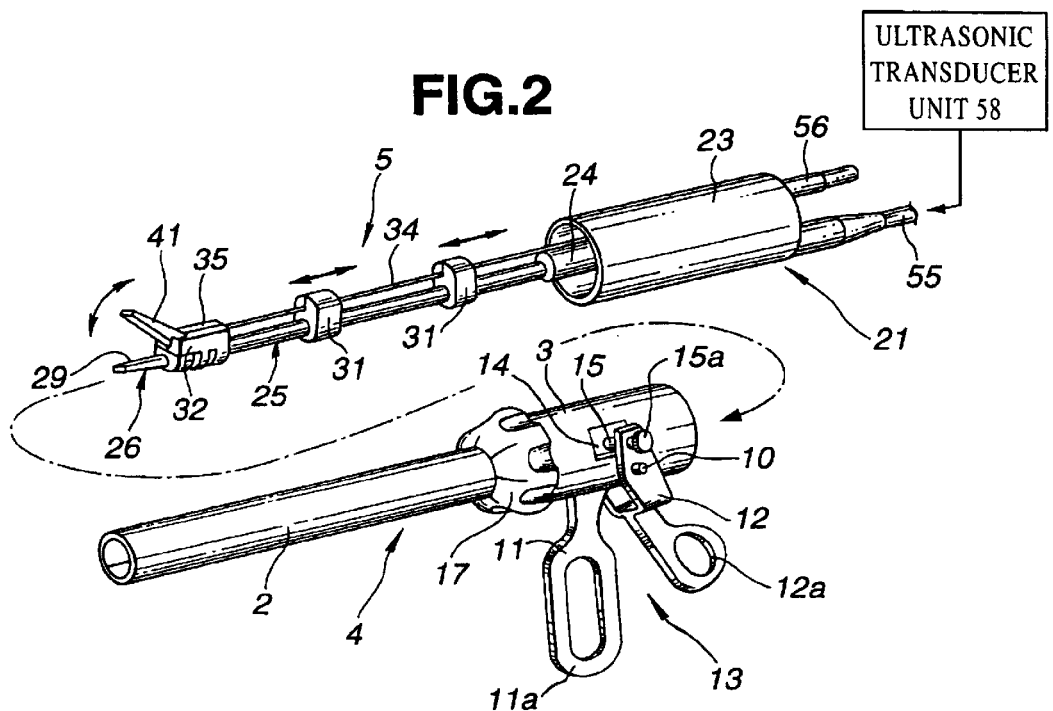
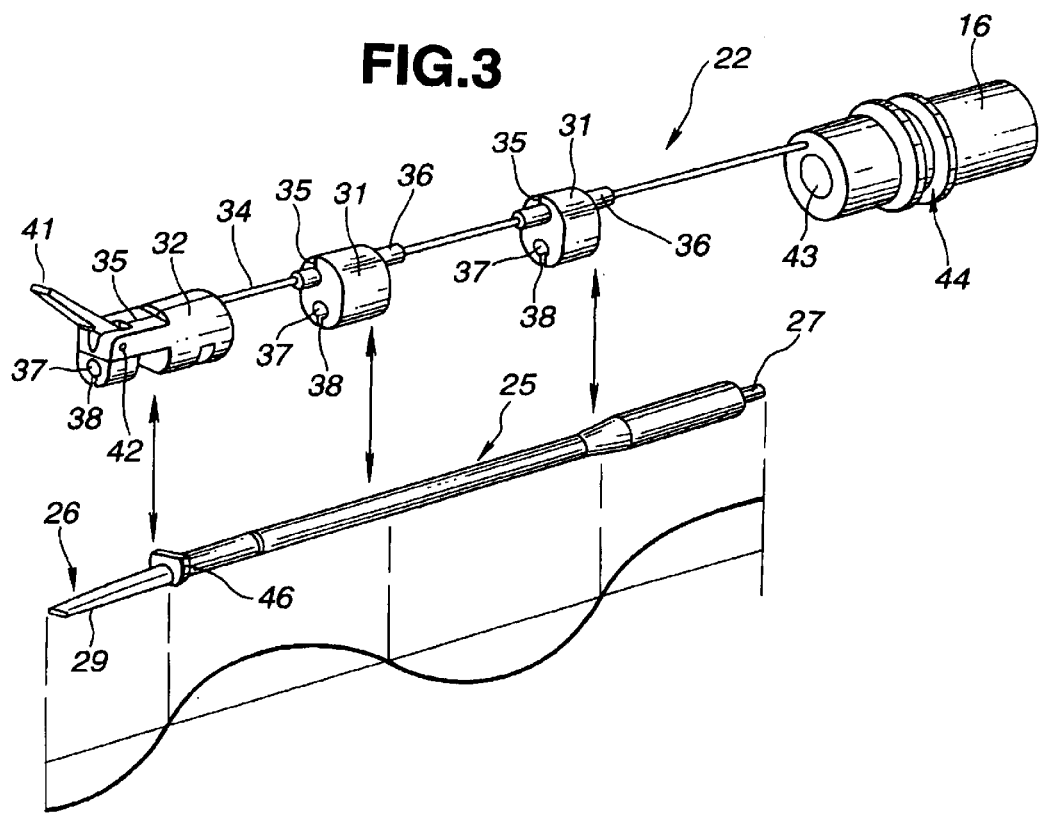

ULTRASONIC TREATMENT APPLIANCE

BACKGROUND OF THE INVENTION

1. Field of the Invention

The present invention relates to an ultrasonic treatment appliance for incising or coagulating a living tissue by utilizing ultrasonic waves with the living tissue clamped by a clamping member.

2. Description of the Related Art

U.S. Pat. No. 5,322,055 has presented an appliance for treating a living tissue ultrasonically. Herein, the living tissue is clamped between the distal part of a probe, which serves as a vibration transmission member, and a clamping member that is opposed to the distal part of the probe and can rotate freely.

This type of ultrasonic treatment appliance clamps a living tissue to be coagulated or resected by the distal part of a probe and a clamping member. The clamped living tissue may be a very soft tissue such as a vessel or the fat or only a small portion of the living tissue may be clamped. In this case, a very large quantity of clamping force is not needed to coagulate or resect the living tissue.

However, for coagulating or resecting a large portion of a tissular region that is relatively hard to resect, such as, a parenchymal organ, for example, the liver or duodenum, a large quantity of clamping force is needed.

In this case, a large bending stress is applied to the probe. This causes the probe to warp in a direction in which the clamping member closes, that is, in a direction in which the probe recedes from the clamping member. In general, the clamping member is designed to press all positions of the probe with the same load. When the clamping member is clamping a living tissue, a uniform load is applied to the probe.

At this time, the magnitude of the bending stress applied to the probe depends greatly on the sectional shape of the clamping member of the probe, that is, a section modulus thereof.

At present, as described in the specification of the U.S. Pat. No. 5,322,055, the sectional shape of a clamping member of a probe is constant relative to the longitudinal direction of the probe.

Now, actual treatment will be discussed.

The smaller the diameter of the probe is, the larger field of view is provided near the probe tip. This permits adroit manipulation for treatment. However, the probe is shaped so that only a small section modulus is exhibited for a normal stress applied to the probe. The probe therefore warps.

Moreover, the outer diameter of an insertion unit of a hand-held piece of the foregoing current ultrasonic treatment appliance is approximately 10 mm. When an attempt is made to design the hand-held piece so that the outer diameter will be, for example, 5 mm or 3 mm, the sectional area of the probe must be made smaller than the current one. At this time, the probe exhibits a much smaller section modulus for a normal stress necessary to coagulate or resect a tissue.

When a probe is shaped to exhibit a constant section modulus, which is smaller than a certain value, over the whole area of the distal part of the probe, a quantity of clamping force, that is, a normal stress becomes large. This causes the probe to warp.

Once a probe warps, when the probe clamps a tissue in cooperation with a clamping member, the probe will not mesh with the clamping member properly. In other words, the roots of the probe and clamping member have such a positional relationship that the tissue cannot be coagulated or resected, because the tissue is sticking to the probe and clamping member. Nevertheless, the tips of the probe and clamping member have such a positional relationship that the tissue cannot be coagulated or resected, because the tips are spaced. This poses a problem of a deteriorated ability to resect a tissue.

Moreover, an operator may handle the probe to limit the movements of the clamping member in an effort to decrease a quantity of applied clamping force. This is intended to prevent the probe from warping and prevent the probe and clamping member from having the positional relationship disabling coagulation and resection. As a result, the quantity of clamping force becomes too small. Consequently, the problem of a deteriorated ability to resect a tissue arises.

Furthermore, there is another problem that especially the top of a probe is prone to a flaw.

For example, another treatment appliance may be held by mistake during an actual surgical procedure or during ultrasonic oscillation. In this case, it is unavoidable that the top of the probe is flawed, though the flow is small.

Moreover, when a burn of a tissue sticks on the top of the probe, it may be removed by performing cleaning after use. In this case, when a sharp cleaning tool is used to scrub the top of the probe, the probe may be flawed.

Moreover, some ultrasonic treatment appliances including the one disclosed in Japanese Unexamined Patent Publication No. 10-127654 have a metallic probe opposed to a clamping member. In this case, the probe and clamping member rubs against each other at every ultrasonic oscillation. The probe may flow.

Any of the ultrasonic treatment appliances has a structure prone to flaw, that is, undergo a small crack near the top of the probe.

Assume that although a small crack has occurred on the top of a probe, the probe is used to clamp a living tissue and vibrated ultrasonically. In this case, a stress is induced by ultrasonic vibration (in this case, the stress becomes maximum at a node of an ultrasonic wave and becomes minimum at an antinode thereof). Moreover, a bending moment is developed in the probe by clamping the tissue. The stress and bending moment are compounded to bring about a situation of stress distribution. In this situation, the actions of all moments work on the flaw on the top of the probe. Especially, the bending moment developed by clamping a tissue acts as a load stress causing the flaw on the top of the probe to develop. If oscillation is repeated in this state, there arises a fear that a fatigue crack occurs with the flaw as a starting point.

Moreover, Japanese Unexamined Patent Publication No. 8-275949 has disclosed an ultrasonic incision/coagulation appliance in which a clamping surface used to reliably clamp a living tissue has an irregular part. In this appliance, the irregular part of the clamping surface acts as a portion on which a stress is concentrated, and thus becomes a factor of a crack. It is therefore impossible to expect improvement in durability of a probe. Besides, when the clamping surface is rubbed against a tissue, since a contact area is limited, frictional heat hardly occurs. This disrupts anticipation of stable coagulation or resection.

Furthermore, ultrasonic incision/coagulation appliances disclosed in Japanese Unexamined Patent Publications Nos. 8-275950 and 9-38099 are analogous to the appliance in the Japanese Unexamined Patent Publication No. 8-275949.

That is to say, a clamping surface used to reliably clamp a living tissue has an irregular part.

Incidentally, even when a solid probe free from a bending moment is vibrated ultrasonically, a fatigue failure will not occur. Moreover, it is experimentally confirmed that even if a small crack occurs, the crack will not develop.

SUMMARY OF THE INVENTION

An object of the present invention is to provide an ultrasonic treatment appliance in which a warp of a probe occurring when a living tissue is clamped is restrained.

Another object of the present invention is to provide an ultrasonic treatment appliance having stable coagulating and resecting abilities.

Still another object of the present invention is to provide an ultrasonic treatment appliance in which the durability of a probe has been improved.

Briefly, an ultrasonic treatment appliance in accordance with the present invention offers stable treatability and enjoys excellent durability. The ultrasonic treatment appliance consists of: an ultrasonic transducer unit having an ultrasonic transducer, which produces ultrasonic waves, incorporated in a hand-held piece; a probe connected to a horn that amplifies ultrasonic waves produced by the ultrasonic transducer, and serving as a vibration transmission member; a treatment member located at the distal end of the probe, having an ultrasonic treatment surface that is parallel to the longitudinal axial direction of the probe and is flat, exhibiting a larger section modulus in the proximal part thereof than in the distal part thereof, and having ultrasonic waves transmitted thereto; a clamping member, opposed to the treatment member, for clamping a living tissue in cooperation with the treatment member; and a clamping manipulation unit for use in moving at least one of the treatment member and clamping member so as to clamp a living tissue between the treatment member and clamping member.

BRIEF DESCRIPTION OF THE DRAWINGS

FIGS. 1 to 11 are diagrams for explaining the first embodiment of the present invention;

FIG. 1 is an oblique view showing an ultrasonic incision/coagulation appliance;

FIG. 2 is an oblique view showing the ultrasonic incision/coagulation appliance with a body of a hand-held piece and a treatment unit thereof separated from each other;

FIG. 3 is a diagram for explaining a clamping member unit and probe of the ultrasonic incision/coagulation appliance;

FIG. 4 is a diagram showing a longitudinal section of a portion near the distal part of the ultrasonic incision/coagulation appliance with the clamping member unit and probe assembled, and also showing the distal part of the probe;

FIG. 5 is a front view of the portion near the distal part of the ultrasonic incision/coagulation appliance;

FIG. 6 is a longitudinal sectional view of the clamping member of the ultrasonic incision/coagulation appliance;

FIG. 7 is a diagram for explaining the distal part of the probe;

FIG. 8 is a diagram showing the relationship between an angle θ and a magnitude of cavitation;

FIG. 9 is a diagram showing a probe having a surface perpendicular to the longitudinal axial direction of the probe;

FIG. 10 is a diagram showing an example of a probe capable of preventing a tissular change stemming from cavitation;

FIG. 11 is a diagram showing another example of a probe capable of preventing a tissular change stemming from cavitation;

FIG. 14 is an oblique view showing the distal part of an ultrasonic incision/coagulation appliance; and FIG. 15 is a diagram showing a warping clamping member.

DESCRIPTION OF THE PREFERRED EMBODIMENTS

Referring to FIGS. 1 to 11, the first embodiment of the present invention will be described below.

This embodiment is an ultrasonic coagulation/incision appliance that is an example of an ultrasonic treatment appliance.

Figure 1:
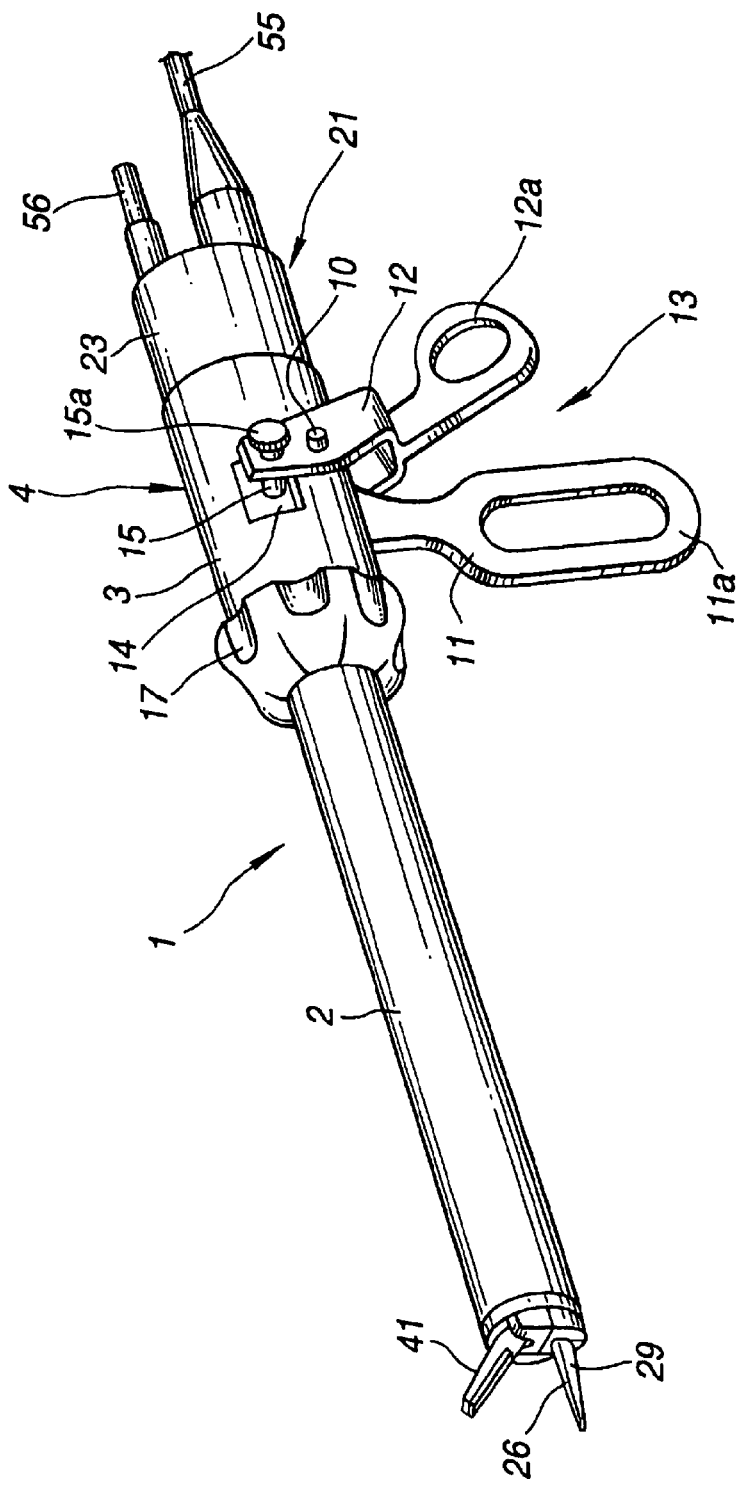

As shown in FIG. 1, an ultrasonic coagulation/incision appliance 1 forms a body 4 of a hand-held piece (treatment appliance body) consisting of an elongated cylindrical sheath 2 that is an insertion unit protecting member, and a cylindrical clamping unit sheath 3 attached to the proximal end of the sheath 2. A treatment unit 5 shown in FIG. 2 is mounted in the body 4 so that the treatment unit can be dismounted freely.

The clamping unit sheath 3 is provided with a clamping manipulation unit 13 that has a stationary handle 11 and movable manipulation handle 12.

The stationary handle 11 is fixed to the clamping unit sheath 3 on a stationary basis. The movable manipulation handle 12 is pivoted to the clamping unit sheath 3 with a pin 10. The stationary handle 11 and movable manipulation handle 12 have annular finger-rest portions 11a and 12a at edges thereof that are turned.

A window 14 is formed to open on one side surface of the clamping unit sheath 3. A locking pin 15 thrust through the upper part of the movable manipulation handle 12 is inserted into the window 14, and engaged with a sliding cylinder 16 of the treatment unit 5 shown in FIG. 3. The sliding cylinder 16 is slid back and forth, whereby a treatment clamping member (movable blade) 41 that will be described later is opened or closed.

The locking pin 15 is screwed into the upper part of the movable manipulation handle 12. By turning a head 15a of the pin 15, the tip of the locking pin 15 can be thrust to be locked in an annular groove 44 on the sliding cylinder 16. On the contrary, the locking pin 15 can be withdrawn to be unlocked from the annular groove 44 on the sliding cylinder 16.

The proximal part of the insertion unit protection sheath 2 is attached to the clamping unit sheath 3 so that it can be turned freely about the axis of the insertion unit protection sheath. A turning knob 17 formed at the proximal end of the insertion unit protection sheath 2 can be used to turn the insertion unit protection sheath 2 about the axis thereof.

The treatment unit 5 consists of an ultrasonic transducer unit 21 and clamping member unit 22.

The ultrasonic transducer unit 21 consists of an ultrasonic transducer, which is not shown, incorporated on a stationary basis in a cover sheath 23 of the body 4 of the hand-held piece, a horn 24, and a probe 25 serving as a vibration transmission member. Ultrasonic waves produced by the ultrasonic transducer are amplified by the horn 24 and transmitted to the probe 25. The probe 25 transmits the ultrasonic waves to an ultrasonic treatment surface (hereinafter simply a treatment surface) 26 formed as the distal part of the probe.

The horn 24 and probe 25 for transmitting waves produced by the ultrasonic transducer are often made of a material exerting a great acoustic effect and well accepted by a living body, such as, titanium or aluminum.

The probe 25 has a screw portion 27 at the proximal end thereof. The screw portion 27 is engaged with the distal part of the horn 24 and thus fastened thereto. The clamping member unit 22 has a plurality of spacers 31 arranged at positions coincident with nodes of an ultrasonic wave. The leading spacer also serves as a clamping member support base 32. A groove 35 in which a manipulation rod 34 that is a member forming a manipulation force transmission medium means is fitted is bored in the upper part of each spacer 31.

Incidentally, reference numeral 55 denotes an ultrasonic driving power cord connected to an ultrasonic transducer unit 58 and 56 denotes a power cord be coupled to a diathermy power supply.

As shown in FIG. 3, an external locking member 36 that is a small-diameter pipe is fitted and locked in each groove 35. The manipulation rod 34 is passed through the external locking members 36 and thus immobilized. A through hole 37 through which the probe 25 is penetrated, and a detachment slit 38 are formed in the lower part of each spacer 31. The probe 25 is inserted into the through holes 37 so that the probe 25 can slide in the axial direction thereof. Each spacer 31 is made of a material permitting smooth sliding, such as, so-called Teflon.

Figure 4:
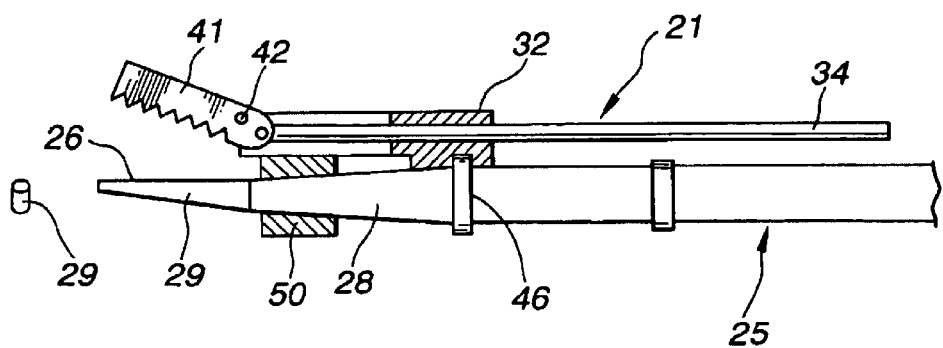

As shown in FIG. 4, a metallic clamping member 41 is opposed to a treatment member 29 that is a stationary blade formed as the distal part of the probe 25. The metallic clamping member 41 is realized with a movable blade for clamping or releasing a living tissue in cooperation with the treatment member 29. The metallic clamping member 41 that works as, say, a jaw is pivoted to the clamping member support base 32 also serving as the leading spacer by means of a pin 42. The tip of the manipulation rod 34 is pivoted to the proximal end of the clamping member 41.

In other words, the clamping member 41 is coupled to the sliding cylinder 16 via the manipulation rod 34 pivoted to the proximal end thereof. The sliding cylinder 16 is moved back and forth. This causes the clamping member 41 to pivot by way of the manipulation rod 34.

As shown in FIG. 3, the sliding cylinder 16 has a passage hole 43 through which the proximal part of the probe 25 is passed. Moreover, an annular groove 44 in which the locking pin 15 of the movable manipulation handle 12 is fitted is formed on the outer circumference of the sliding cylinder 16.

The sliding cylinder 16 is passed through the clamping unit sheath 3 so that it can freely slide back and forth. The clamping member 41 opposed to the treatment surface 26 can be opened or closed by turning the movable manipulation handle 12.

On the other hand, a collar 46 shaped to be, for example, rectangular is located at a position coincident with a node of an ultrasonic wave which is a position at the extreme tip of the probe 25. The collar 46 is locked in the lower part of the clamping member support base 32 in the drawing.

Figure 5:
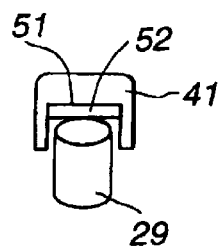

Moreover, the cross section of a metallic body member of the clamping member 41 is, as shown in FIG. 5, shaped like a bracket. A clamping groove 51 is formed in the body member. A thin chip 52 that is a thin metallic plate is placed on the bottom of the clamping groove 51. The thin chip 52 placed on the bottom of the clamping groove 51 meets the blade portion (upper surface) of the treatment member 29.

Figure 6:
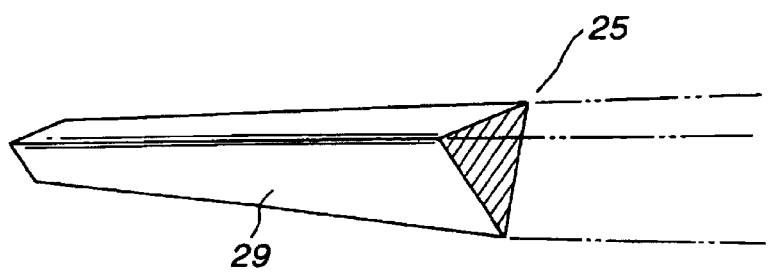

In other words, the treatment member 29 has the ultrasonic treatment surface 26 that is a blade portion opposed to the clamping member 41. The ultrasonic treatment surface 26 for clamping a living tissue in cooperation with the clamping member 41 is a flat surface. The treatment member 29 is shaped so that at least the longitudinal section thereof will get larger gradually from the tip thereof toward the root thereof. The shape of the longitudinal section is substantially rectangular. Alternatively, the shape may be, as shown in FIG. 6, inversely triangular or semi-circular.

When a living tissue is clamped between the treatment member 29 and clamping member 41, the clamping member 41 applies a uniform load to the treatment member 29 of the probe 25. Consequently, a bending stress incurred by the treatment member 29 increases gradually from the tip thereof towards the root thereof.

Owing to the foregoing longitudinal sectional shape, a section modulus in the treatment member 29 of the probe 25 increases gradually from the tip thereof towards the root thereof. This is effective in suppressing a stress to be applied to the treatment member 29. In this case, the probe 25 should preferably be designed not to warp.

A portion of the probe 25 serving as the ultrasonic action surface 26 of the treatment member 29 will not warp. Therefore, when a tissue is clamped, frictional heat is developed in the living tissue clamped between the probe 25 that is vibrating ultrasonically and the clamping member (immobile clamping member) 41. When the frictional heat is used to coagulate or resect the clamped living tissue, the clamped portion of the living tissue can entirely be coagulated or resected on a stable basis. This means that stable and secure treatment is possible.

Moreover, even if a small crack or the like occurs on the top of the probe 25, an excess bending stress will not be developed in the probe 25. Any stress will therefore not grow to a load stress causing a fatigue crack. The probe 25 will therefore not be broken. The durability of the probe 25 is thus improved drastically.

Figure 7:
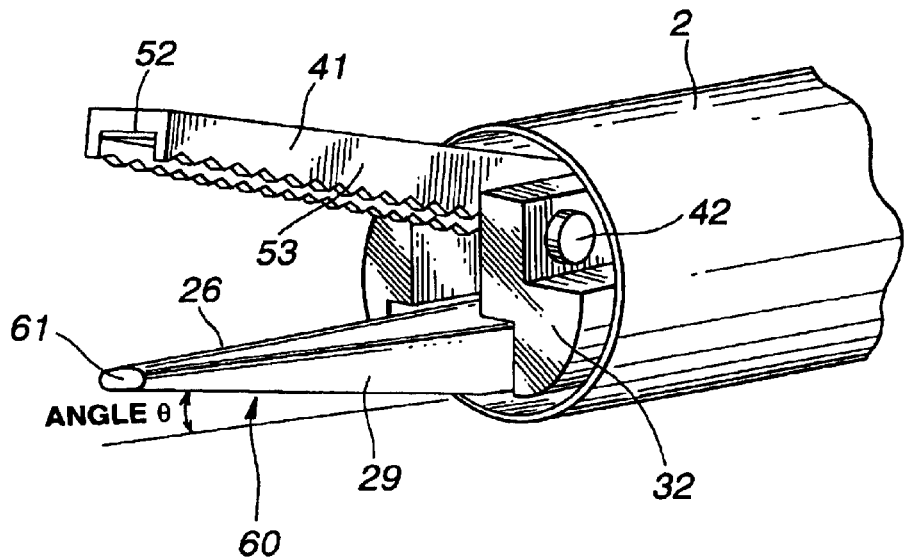

Moreover, as shown in FIG. 7, an angle created between a lower surface 60 and the longitudinal axial direction of the probe 25 is θ. Herein, the lower surface 60 is shaped so that a section modulus exhibited by the treatment member 29 of the probe 25 will increase gradually from the distal end of the treatment member towards the proximal end thereof. Depending on whether the angle θ is large or small, an adverse effect on treatment varies.

Specifically, the angle θ between the lower surface 60 and the longitudinal axial direction of the probe 25 brings about cavitation without fail. The cavitation is regarded as a means useful in crashing a tissue in an ultrasonic suction appliance or the like. However, the cavitation is a means employed during a surgical procedure. In the case of an ultrasonic coagulation/incision appliance, cavitation occurring at an unexpected position not only hinders treatment but also causes an unacceptable change in tissue.

In particular, the lower surface 60 lies at a position liable to come out of an operator's visual range. There is a strong possibility that the lower surface 60 will approach a living tissue too closely or meet it. If cavitation is induced by the lower surface 60 located at the position, a tissue near the lower surface 60 may change.

At a position perpendicular to the direction of propagation of an ultrasonic wave, or, at an angle θ of 90° in this drawing, cavitation becomes most intense and occurs most frequently. As the angle θ gets smaller, that is, an inclination decreases, the frequency of occurrence of cavitation decreases.

An experimentation demonstrates that a tissular change stemming from cavitation poses a problem in the range of 50°<θ<90°. The angle θ should therefore be equal to or smaller than 50°, or preferably, set to 30° or smaller. Thus, the problem of a tissular change stemming from cavitation is solved, and the drawback of changing a tissue near the lower surface 60 is resolved. Eventually, reliable and secure therapy can be achieved.

Now, the details of the experiment will be described with reference to FIG. 7.

For the experiment, four types of probes 25 that were mutually different in angle θ created between the lower surface 60 and the longitudinal axial direction of a probe 25 were procured. The angles θ relative to the employed probes 25 were 90°, 70°, 50°, and 30°. The four types of probes 25 were vibrated ultrasonically in water.

The ultrasonic frequency was 23.5 kHz. The amplitude was a maximum output value of an employed ultrasonic transducer, that is, 200 μm. The maximum output value was the largest value of output values generally adopted for coagulation or incision that was the main ability of the ultrasonic coagulation appliance.

Cavitation occurring in the above state was observed using a color Doppler ultrasonic observation apparatus. The observation apparatus enabled observation of cavitation in colors. Cavitation could therefore be assessed quantitatively.

Figure 8:
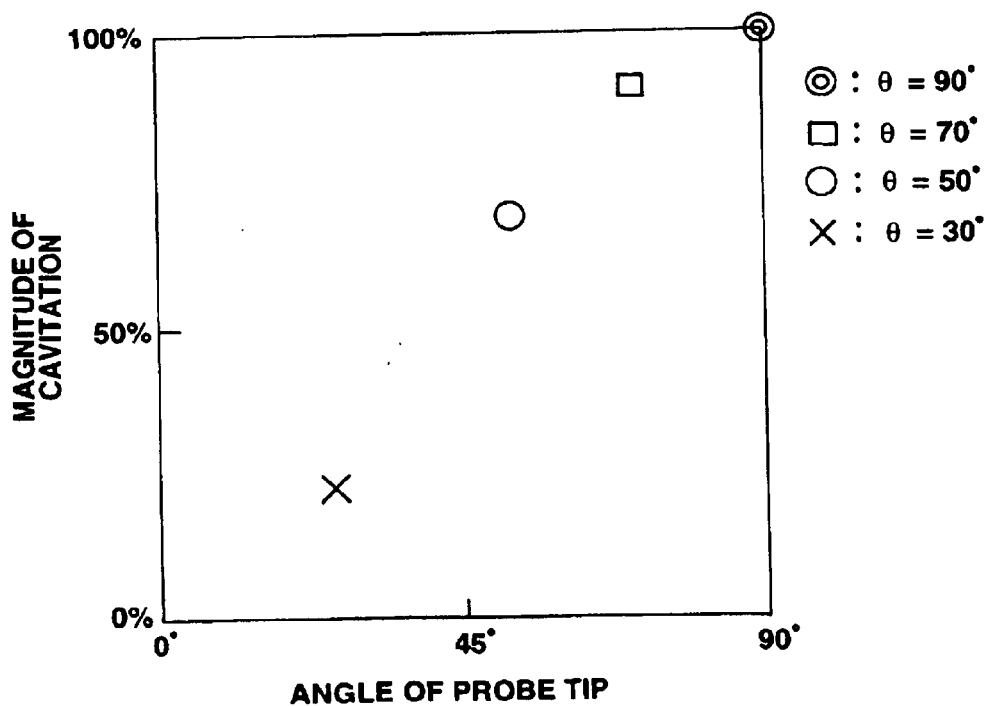

Measured first was a magnitude of cavitation induced by a probe 25 that was supposed to induce the largest magnitude of cavitation and that created the angle θ of 90°. The measured magnitude of cavitation was used as a reference. In FIG. 8, the reference magnitude of cavitation is associated with 100%.

Thereafter, a magnitude of cavitation at each angle θ was measured. A ratio of each magnitude of cavitation to the magnitude of cavitation measured at the angle θ of 90° was calculated. Ratios of magnitudes of cavitation to the magnitude of cavitation measured at the angle θ of 90° were plotted as shown in FIG. 8. The resultant curve demonstrates that as the angle θ gets smaller, the magnitude of cavitation decreases.

Furthermore, a portion of each of the probes that were mutually different in angle θ, which induced cavitation, was approached to a tissue. A magnitude of cavitation and a tissular change were checked visually.

When the probes creating the angles θ of 90° and 70° indicated with ⊚ and □ in FIG. 8 were approached to the tissue, the surface of the tissue changed apparently or bled in several seconds.

When the probe creating the angle θ of 50° indicated with ○ was approached to the tissue, the surface of the tissue hardly changed with the passage of time.

When the probe creating the angle θ of 30° indicated with x was approached to the tissue, unless the probe met the tissue, the surface of the tissue showed no critical change.

In short, when a probe is approached very close to a tissue, the tissue changes or does not change depending on the angle θ.

Moreover, it was confirmed that when the amplitude was varied from a large value to a small value, similarly to when the angle θ was varied from a large value to a small value, a tissue changed. This is not graphically illustrated, though.

In other words, the value of the angle θ and the value of the amplitude dominate the magnitude of cavitation.

In the experiment, only one frequency was adopted. In a relatively low frequency band of 60 kHz or less employed in a typical ultrasonic coagulation/incision appliance, cavitation is generally thought to occur at almost the same level (sound intensity of 1 W/in or less).

The relationship illustrated in FIG. 8 is therefore thought to remain in an ultrasonic coagulation/incision appliance irrespective of a frequency. Setting the angle θ to 50° or less is effective in resisting a tissular change stemming from cavitation.

Figure 9:
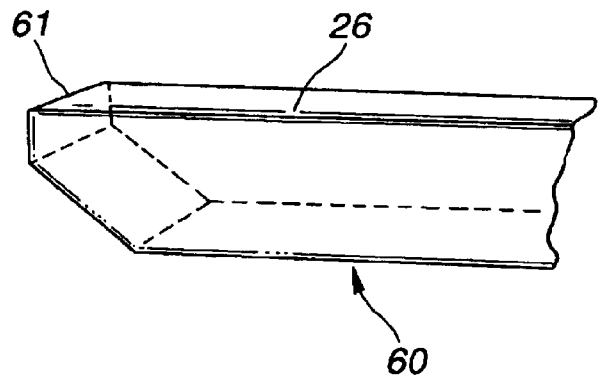

When the probe 25 has, as shown in FIG. 9, a surface 61 perpendicular to the longitudinal axial direction of the probe 25, intense cavitation is induced by the vertical surface 61. Most preferably, therefore, the vertical surface 61 should not be formed on the probe 25.

Figure 10:
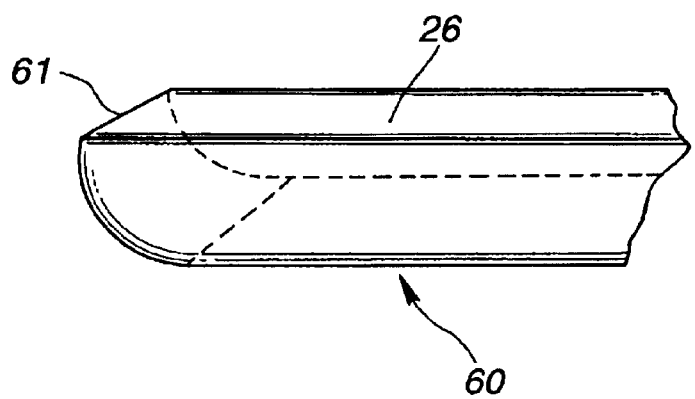
Figure 11:
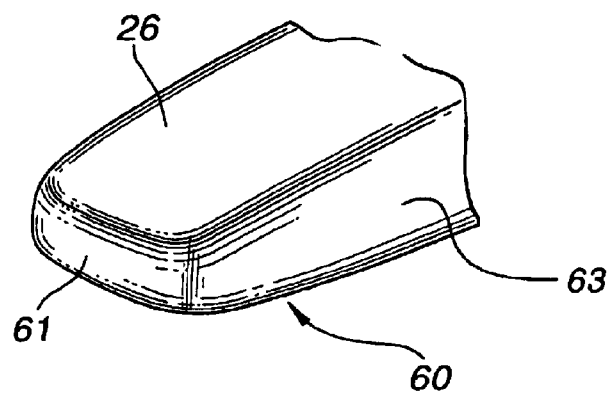

An angular edge created between the lower surface 60 and vertical surface 61, or an angular edge created between an upper surface 62 of a probe and the vertical surface 61 may be, as shown in FIG. 10, chamfered to be a curved surface. The lower surface 60, vertical surface 61, and upper surface 62 may thus be linked in a streamlined fashion. Otherwise, angular edges created between side surfaces 63 of the probe and the vertical surface 61 thereof may, as shown in FIG. 11, be chamfered to be curved surfaces. The side surfaces and vertical surface may thus be linked in a streamlined fashion. When the vertical surface 61 is made smaller or eliminated, a tissular change stemming from cavitation can be prevented.

Consequently, it becomes unnecessary to sharpen a probe tip for preventing occurrence of cavitation.

Moreover, as shown in FIG. 6, when the cross sectional shape of the treatment member 29 of the probe 25 is inversely triangular, the lower side surfaces are angled. A wide field of view can therefore be provided in front of the distal end of the clamping member. A delicate tissue can be treated successfully.

Figure 12:
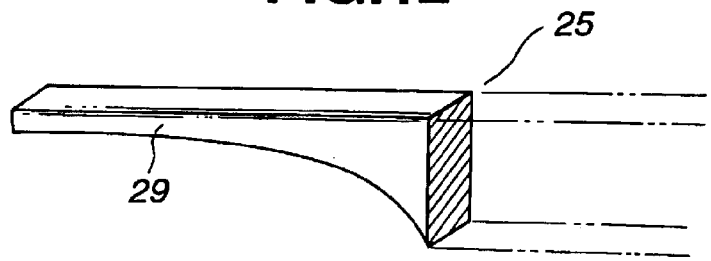
FIG. 12 is a perspective view showing a clamping member of an ultrasonic incision/coagulation appliance in accordance with the second embodiment of the present invention.

Referring to FIG. 12, the second embodiment of the present invention will be described below.

The second embodiment provides a variant of a treatment member. The other components are identical to those of the first embodiment.

As illustrated, the longitudinal sectional shape of the treatment member 29 of the probe 25 is a shape whose lower side is a curve progressively descending from the tip of the treatment member towards the root thereof. Preferably, the longitudinal sectional shape is a shape whose lower side is an exponential curve, or a shape whose area increases as an exponential function.

A theoretical bending stress developed in the probe 25 when a uniform load is applied to the probe 25 is plotted as an exponential curve. The exponential curve represents an exponential function in relation to positions from a position at the distal end of the probe to a position at the root thereof at which the load is applied. Even in this case, an increase in value of a section modulus exhibited by the probe 25 is proportional to a change in stress. From this viewpoint, this embodiment can be said to be more preferable than the first embodiment. Moreover, a bending stress developed in the probe 25 can be suppressed strictly. The risk of a fatigue failure can be alleviated more successfully.

Figure 13:
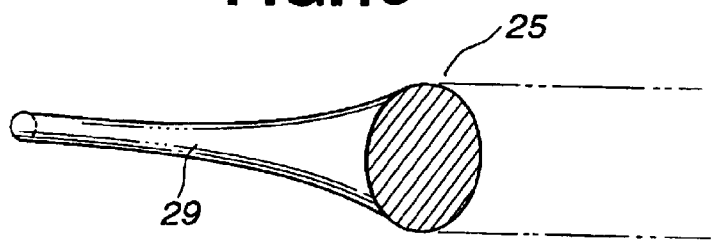
FIG. 13 is a perspective view of a clamping member of an ultrasonic incision/coagulation appliance in accordance with the third embodiment of the present invention.

Referring to FIG. 13, the third embodiment of the present invention will be described below.

The third embodiment provides a variant of a treatment member of a probe. The other components are identical to those of the first embodiment.

As illustrated, the cross sectional shape of the treatment member 29 of the probe 25 is a circle whose diameter gets larger from the distal end of the treatment member towards the root thereof. The cross sectional area increases progressively, or preferably, increases exponentially.

A theoretical bending stress developed in the probe 25 when a uniform load is applied to the probe 25 is plotted as an exponential curve. The exponential curve represents an exponential function in relation to positions from a position at the distal end of the probe towards the root thereof at which the load is applied. Even in this case, an increase in value of a section modulus exhibited by the probe is proportional to a change in stress. From this viewpoint, this embodiment can be said to be more preferable than the first embodiment. Moreover, a bending stress developed in the probe 25 can be suppressed strictly. Consequently, the risk of a fatigue failure can be alleviated more successfully.

Figure 14:
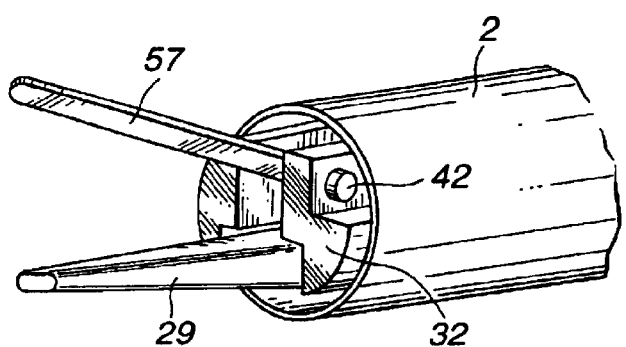
FIGS. 14 and 15 are diagrams for explaining the fourth embodiment of the present invention.
Figure 15:
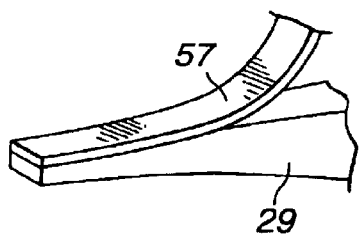

Referring to FIGS. 14 and 15, the fourth embodiment of the present invention will be described below.

The fourth embodiment provides a variant of a treatment member of a probe. The other components are identical to those of the fourth embodiment.

As shown in FIG. 14, in this embodiment, a clamping member 57 is realized with a plate spring. When the clamping member 57 is pressed against the treatment member 29 of the probe 25, the clamping member 57 warps as shown in FIG. 15. An excess load will therefore not be applied to the treatment member 29 of the probe 25.

Owing to the above structure, the probe 25 will not warp. Moreover, the distal part of the clamping member 57 can be made thinner. A wider field of view can be provided.

According to the present invention, it is apparent that a wide range of different embodiments can be constructed based on the invention without a departure from the spirit and scope of the invention. This invention will be limited to the appended claims but not be restricted to any specific embodiments.

What is claimed is:

1. An ultrasonic treatment appliance offering stable treatability and enjoying excellent durability, comprising:

an ultrasonic transducer unit having an ultrasonic transducer, which produces ultrasonic waves, incorporated in a hand-held piece;

a probe connected to a horn for amplifying ultrasonic waves produced by said ultrasonic transducer, and serving as a vibration transmission member, wherein an angle between a lower surface and longitudinal axis of said probe is at most about 50°;

a treatment member located at a distal end of said probe, having an ultrasonic treatment surface that is parallel to the longitudinal axial direction of said probe and is flat, with a continuously smooth surface, from a proximal end to a distal end of said treatment member, exhibiting a larger section strength modulus at the proximal end of said treatment member than at the distal end of said treatment member, wherein said treatment member receives ultrasonic waves, and wherein said treatment surface extends along the longitudinal axial direction and has a reduced thickness towards the distal end of said treatment member;

a clamping member, opposed to said ultrasonic treatment surface that is flat of said treatment member, for clamping a living tissue in cooperation with said treatment surface;

a support member which supports said clamping member so that said treatment member is vibrated ultrasonically relative to said clamping member by the ultrasonic waves received from said probe; and a clamping manipulation unit for use in moving said clamping member onto said flat, continuously smooth ultrasonic treatment surface of said treatment member so as to clamp a living tissue between them, wherein when a living tissue is clamped between said clamping member and treatment member, said clamping member warps.

2. An ultrasonic treatment appliance according to claim 1, wherein section modules exhibited by said treatment member increases continuously from the distal end of said treatment member towards the proximal end of said treatment member.

3. An ultrasonic treatment appliance according to claim 2, wherein said treatment member has an outer surface that forms a shape of said treatment member such that the section modulus of said treatment member changes from the distal end of said treatment member towards the proximal end of said treatment member.

4. An ultrasonic treatment appliance according to claim 3, wherein when said treatment member has a surface orthogonal to the longitudinal axis of said probe, an angular edge created by the orthogonal surface and a surface crossing the orthogonal surface is chamfered to be a curved surface.

5. An ultrasonic treatment appliance according to claim 2, wherein said treatment member has a surface that causes the section modulus to change continuously in the form of a curve from the distal end thereof towards the proximal end thereof.

6. An ultrasonic treatment appliance according to claim 5, wherein when said treatment member has a surface orthogonal to the longitudinal axis of said probe, an angular edge created between the orthogonal surface and a surface crossing the orthogonal surface is chamfered to be a curved surface.

7. An ultrasonic treatment appliance according to claim 1, wherein said clamping member is connected to said probe at nodes of an ultrasonic wave.

* * * * *